United States Patent
Hainfeld

(10) Patent No.: US 6,534,039 B2
(45) Date of Patent: Mar. 18, 2003

(54) EXTENDED ORGANIC COBALT AND NICKEL MAGNETIC COMPLEXES

(76) Inventor: James F. Hainfeld, 44 Bradley Dr., Shoreham, NY (US) 11786

( * ) Notice: Subject to any disclaimer, the term of this patent is extended or adjusted under 35 U.S.C. 154(b) by 17 days.

(21) Appl. No.: 09/834,049

(22) Filed: Apr. 11, 2001

(65) Prior Publication Data

US 2002/0028993 A1 Mar. 7, 2002

Related U.S. Application Data

(63) Continuation-in-part of application No. 09/621,185, filed on Jul. 21, 2000.
(51) Int. Cl.$^7$ ............................................... A61B 5/055
(52) U.S. Cl. ................... 424/9.32; 424/9.323; 424/9.36
(58) Field of Search ................ 424/9.3, 9.32, 424/9.322, 9.323, 9.36

(56) References Cited

U.S. PATENT DOCUMENTS

| | | |
|---|---|---|
| 4,795,626 A | 1/1989 | Deutsch et al. |
| 5,521,289 A | 5/1996 | Hainfeld et al. |
| 5,858,329 A | 1/1999 | Peng et al. |
| 5,879,659 A | 3/1999 | Edwards et al. |

*Primary Examiner*—Michael G. Hartley
(74) *Attorney, Agent, or Firm*—Pierce Atwood; Kevin M. Farrell

(57) ABSTRACT

Disclosed is a method for in vivo imaging tissue of a individual, by performing magnetic resonance imaging utilizing an extended cobalt complex as a contrast enhancement agent. The extended cobalt complex is comprised of cobalt atoms, a carboxylate ligand, an amine ligand, and a multidentate thiol-containing organic ligand, the cobalt atoms being linked to thiol groups and counter ions. The extended cobalt complex is characterized as stable, water soluble, non-aggregating, magnetic, and from 0.5 to 10 nm in size. This method is especially useful in imaging tumor tissue, and also tissue which is regenerating from a wound. The extended cobalt complex can be specifically targeted to a particular tissue to enable selective imaging of that tissue. This is done by linking the extended cobalt complex to a binding moiety which specifically binds a molecule selectively expressed in the tissue. Also disclosed is a method for visually detecting the presence of an antigen in a sample using an antibody which specifically binds the antigen, the antibody being coupled to an extended cobalt complex. In the method, the antibody is contacted to the sample under conditions appropriate for antibody-antigen binding, and the presence of the extended cobalt complex which is bound to the antigen is detected by its characteristic color or its magnetic properties.

16 Claims, No Drawings

EXTENDED ORGANIC COBALT AND NICKEL MAGNETIC COMPLEXES

RELATED APPLICATIONS

This is a continuation-in-part of U.S. patent application Ser. No. 09/621,185, EXTENDED ORGANIC COBALT AND NICKEL MAGNETIC COMPLEXES, filed on Jul. 21, 2000, the contents of which are incorporated herein by reference.

BACKGROUND OF THE INVENTION

Magnetic materials have many utilities including use in computer disk memory storage, audio and video recording tape, sensors, coatings, magneto-optical devices, as magnetic resonance imaging (MRI) contrast enhancement agents, and biolabels for molecular or cell tagging or separations. Typically iron oxides, hematite, $Fe_2O_3$, maghemite, gamma-$Fe_2O_3$ and magnetite, $Fe_3O_4$ are used, or various alloys, such as in alnico magnets (aluminum, nickel, cobalt), or mixed oxide materials with octahedral $Fe^{3+}$ ions such as, the spinels $BaFe_{12}O_{19}$ and $Ba_2Mn_2Fe_{12}O_{22}$, used in magnetic tapes. Gadolinium, complexed with DTPA (diethylenetriamine pentaacetic acid), Gd-DTPA, is commonly used for MRI enhancement.

Unfortunately, currently available magnetic materials have a number of shortcomings which limit the potential of the applications in which they are used. For example, magnetic recording media is far below its potential density due to a lack of precise control in preparing and magnetically isolating storage bits, and organizing regular smaller elements into arrays. This is largely because the recording media is generated by annealing bulk coatings which form irregular domains. In order to provide adequate information isolation, larger than desired areas must be assigned to each information bit. If the magnetic recording media was instead constructed from optimally sized magnetic nanoparticles, higher recording densities could be utilized without detracting from overall quality. In the medical field, iron oxide nanoparticles used as imaging agents are irregular in size, have associated toxicity, and have irregular biodistributions when administered in vivo. The accepted MRI contrast enhancement agent, Gd-DTPA, has a short half-life in the bloodstream, which precludes uses which require longer visualization periods. Also, when Gd-DTPA is conjugated to a targeting moiety, such as an antibody, imaging signal generated at the target is too weak to be generally useful for targeted imaging of, for example, tumors, clots, or atherosclerotic plaques. The therapeutic application of oscillating magnetic fields to magnetic particles, such as iron distributed at a site in the body, has been proposed for use in heating tumors to destroy them. Success however, has been limited by poor specific tumor uptake of particles, lack of sufficient particle accumulation, and commensurate particle toxicity.

The synthesis of magnetic nanoparticles generally involves grinding of macroscopic magnets, sonication, the formation of micelles, pH adjustment, or controlled oxidation. Unfortunately, these presently used methods produce heterogeneously sized particles which are suboptimal or precludes their use in many applications. There is a need in the related arts for uniform, small magnetic materials, especially less than 10 nm.

The magnetic nanoparticles currently available in the art usually aggregate during formation and use, as evidenced from electron micrographs of the material. Aggregation is an undesirable property. An additional undesirable property is a lack of stability of the magnetic materials. Magnetic particles in the art exhibit altered and degraded magnetic properties after short periods of storage. Many iron particles continue to oxidize, as is common with rusting.

It is often necessary to further modify the magnetic particles prior to use. For instance, many magnetic materials must be coated. Coating is by mixing the particle with sugars, polymers and various other substances. These coatings suffer from the instability of adsorption. Another modification is the covalent attachment of molecules to the particles. One example is the attachment of a molecule to the oxygen atom of an iron oxide particle. Although the produce has a covalent linkage, which is useful for many applications, there are many other drawbacks associated with utilizing iron particles as magnetic material, such as instability, poor size distributions, toxicity and aggregation, which limits use.

SUMMARY OF THE INVENTION

One aspect of the present invention is a method for in vivo imaging an internal component of an individual, such as tissue, utilizing an extended cobalt complex as a contrast enhancement agent. The extended cobalt complex is comprised of cobalt atoms, a carboxylate ligand, an amine ligand, and a multidentate thiol-containing organic ligand, the cobalt atoms being linked to thiol groups and counter ions. The cobalt extended complex is characterized as stable, water soluble, non-aggregating, magnetic, and from 0.5 to 10 nm in size. The method comprises administering the extended cobalt complex to the individual to contact the tissue with the extended cobalt complex, and performing magnetic resonance imaging on the individual to image the tissue. In one embodiment, the tissue which is imaged is a tumor. This method is highly useful for clinical diagnosis of a tumor. In another embodiment, the tissue is regenerating from a wound. The extended cobalt complex is optionally linked to a biomolecule, preferably a binding moiety which specifically targets the extended cobalt complex to a target molecule selectively expressed on the tissue which is to be imaged.

Another aspect of the present invention relates to a method for visually detecting the presence of an antigen in a sample using an antibody which specifically binds the antigen, the antibody being coupled to an extended cobalt complex which has a characteristic color. In the method, the antibody is contacted to the sample under conditions appropriate for antibody-antigen binding, the sample is washed to remove unbound antibody, and the presence of the remaining extended cobalt complex is visually detected by its characteristic color.

DETAILED DESCRIPTION OF THE INVENTION

Aspects of the present invention relate to the development of a new class of organic magnetic material in the form of nanoparticles, which contains nickel and/or cobalt. Magnetic nanoparticles of the prior art are solid particles of magnetic material, such as cobalt or iron oxide. Such particles are either used as is, or coated, for example, with dextrans. At the other end of the size spectrum are single magnetic ions complexed with various organic molecules, such as gadolinium-DTPA. In the present invention, a magnetic nanoparticle composition is synthesized from a small peptide containing a thiol group (referred to herein as a thiol-containing peptide, or a thiol peptide) and various counter ions (referred to also as ligands) to form an extended complex in which multiple cobalt or nickel atoms are linked with multiple peptides such that the apparent molecular weight is greater than about 3,000 daltons (as gauged by exclusion on a gel filtration column with water as the eluent). The extended complex does not pass through a 3,000 molecular weight (nominal) filter (Amicon Centricon 3), but mostly passes through a 10,000 molecular weight filter (Amicon Centricon 10). The complex formed is termed "extended" or "large" because it is much larger in size than low molecular weight complexes, such as Gd-DTPA (molecular weight of 548).

Another aspect of the present invention relates to the method of synthesis of the extended complex. Unlike existing methods for synthesis of magnetic materials, which use sonication, micelles, strong reducing agents, grinding, oxidation, or simple complexion, cobalt or nickel metal salts are complexed with a thiol peptide (glutathione), citrate, ammonia, and chloride in basic solution to form the extended complex. This method was discovered fortuitously while searching for a novel form of magnetic nanoparticle. The method described herein is a refinement of the original procedure During synthesis, an instant color change of the solution from light red or pink to dense, almost opaque brown, without precipitation, occurs when synthesizing extended cobalt complexes. Color change from green to dense, almost opaque brown, without precipitation, occurs when synthesizing extended nickel complexes. The observed color changes were initially unexpected. The resulting color and optical density change of the material indicates plasmon interactions of closely spaced metal atoms or alterations in complexing ligands. Also unexpected was the finding that the extended complex produced from the synthesis reaction was significantly larger than any of the starting reactants, and that it possessed the magnetic properties described herein.

The extended organic cobalt and/or nickel magnetic complex is composed of metal ions Co (II) and Ni (II) complexed with a thiol-containing multidentate bridging ligand ("multidentate thiol-containing organic ligand"), and carboxylate and amine ligands to form a product which is significantly larger than the individual starting components. Other ligands may also be incorporated into the rich, multi-ligand extended complex, for example, chloride or hydroxide ions. Hydrodynamic measurements indicate that the brown-colored complex, produced by methods detailed in the Exemplification section below, has a molecular weight that appears to be in the range of 3,000 to 20,000.

A multidentate bridging ligand is used in the formation of the extended complex. In a preferred embodiment, the thiol peptide glutathione is used. In addition, amine and carboxylate ligands, preferably ammonia from ammonium ions in basic solution, and citrate from trisodium citrate, are also used.

Glutathione is a tripeptide, consisting of gamma-glutamic acid-cysteine-glycine. This provides amine, carboxyl and thiol ligands that coordinate to the metal which typically has 6 coordination sites. This means that a bridging coordination complex can be formed, to produce the "extended" or multimeric complex of the present invention. Glutathione contains several reactive groups: amine, carboxyl, and thiol, useful for crosslinking to other molecules, thus enabling the formation of conjugates.

The extended complex therefore contains multiple species coordinated to the metal atoms. During or after synthesis of the complex, an additional molecule can be substituted for one of these ligands, resulting in direct incorporation or conjugation of the substituted molecule to the extended complex. For example, it was found that Fab' antibody fragments could be stably incorporated into the complex if they are present during complex formation. This aspect of the present invention is described in greater detail below.

The extended complex of the present invention can also be synthesized using analogous substances to the above identified components. For example, any multidentate ligand that is capable of forming an extended complex by bridging metal ions (e.g., peptides or polymers) might be used in place of glutathione. Also, coordinating ligands, such as ammonia and citrate, can be replaced with other substances which similarly coordinate with the metals. Some commonly known ligands for cobalt and nickel which may be used in place of ammonia and citrate are $I^-$, $Br^-$, $Cl^-$, $SCN^-$, $F^-$, urea, $OH^-$, acetate, oxalate, water, $NCS^-$, glycine, pyridine, ammonia, ethylene diamine, $SO_3^{2-}$, dipyridine, o-phenanthroline, $NO_2^-$, and $CN^-$.

The following steps can be used to prepare a cobalt organic complex, a nickel organic complex, or a combination of cobalt and nickel organic complex:

1. A salt of the appropriate metal is dissolved in water; a preferred cobalt salt is cobalt chloride, a preferred nickel salt is nickel sulfate. A solution containing both cobalt and nickel is used to produce a mixed metal complex.
2. A base is prepared; preferred bases are ammonium hydroxide and sodium hydroxide.
3. An aqueous solution of a multidentate thiol-containing organic ligand is prepared; a preferred material is the peptide glutathione.
4. An amine ligand is prepared; a preferred source is an aqueous solution of ammonium chloride (this can be omitted if ammonium hydroxide is used for the base).
5. A carboxylate ligand is prepared; a preferred source is an aqueous solution of trisodium citrate.
6. The above solutions are combined to produce the extended organic cobalt and/or nickel complex; a preferred order of addition is: citrate solution added to the cobalt and/or nickel solution, followed by addition of ammonium hydroxide, and then the thiol peptide. This order maintains everything in soluble form, without precipitates. The order of addition may be varied to produce an essentially similar product, but this may also produce intermediate precipitates.

A preferred pH of the final preparation for complex formation is 9–10. The amounts and concentrations of the various components are important since outside of some range, the extended complex does not form, or alternatively, extensive aggregation occurs. Preferred amounts are 20% (by weight) $CoCl_2.6 H_2O$ or $NiSO_4.6 H_2O$ in 0.4 ml $H_2O$, 20% $Na_3C_6H_5O_7.2 H_2O$ in 0.4 ml $H_2O$, 0.4 ml of 2 M $NH_4OH$, and 0.15 ml of 8% glutathione. A preferred final concentration of components used is: 120 mM of cobalt or nickel ions, 100 mM of citrate ions, 20 mM of glutathione, and 0.3 M ammonium hydroxide. Alternatively, the 0.3 M ammonium hydroxide may be replaced with 0.5 M ammonium chloride and 0.3 M sodium hydroxide. Volumes may of course be scaled to produce more or less product. Variation of the different components to some extent around these values will still result in the same or similar product. Excess components not incorporated into the complex may be separated by gel filtration, chromatography, or other techniques known in the art. Successful preparations may be made by scaling these concentration values within limits, keeping the relative values the same. The preferred molar ratio of components is: 1 mole glutathione: 6 moles cobalt or nickel: 5 moles citrate: 15 moles ammonium hydroxide. Ranges of these components useful for forming the extended complex include: 4 to 8 moles cobalt and/or nickel salts, 0.6 to 1.5 moles multidentate thiol-containing organic ligand, 8 to 30 moles amine ligand, and 3 to 7 moles carboxylate ligand, although other combinations are possible.

Surprisingly, the formed complex has an apparent hydrodynamic molecular weight between 3,000 to 20,000 daltons, far greater than any of the starting components. The weights of the preferred starting components are: $CoCl_2.6\ H_2O$: 238; $Na_3C_6H_5O_7.2\ H_2O$: 294; $NH_4OH$: 35; glutathione: 309.

The above described procedure produces extended complexes which range in size from 0.5 to 10 nm, typically 0.5 to 5 nm. Complexes from 5 to 20 nm can be obtained by decreasing the amount of thiol complexing agent in the preparation. This results in particles that are orange or red in color, rather than brown.

Cobalt and nickel may be combined in the preparation to produce a complex with a mixed composition of magnetic atoms, by mixing proportional amounts of the cobalt and nickel salts during synthesis. Such hybrid particles produced will possess unique magnetic properties. In addition, other metals can also be incorporated. The extended complex described above, which contains cobalt, nickel, or a combination of cobalt and nickel, is suitable for use in the methods described herein. Unless otherwise stated, the term "extended complex" encompasses the extended cobalt complex, nickel extended complex, and cobalt and nickel alloy extended complex.

The extended complex is characterized by several properties which it exhibits. It is highly water soluble and can be dried and then resuspended easily in water, with no apparent alteration. Examination of the complexes formed in a synthesis reaction by electron microscopy indicates they are structures of about 0.5 to 5 nm in size, where the metal is fairly evenly distributed over each complex, rather than having the metal as a dense solid core, giving it a relatively uniform density over its extent. No aggregation of the complexes is detected.

Magnetic measurements taken of a water solution of the cobalt complex show the magnetic field, M, vs. magnetic field strength, H, to be a straight line with a shallow slope up to 13,000 Gauss, giving no indication of ferromagnetism or superparamagnetism. The molar susceptibility of the material is low, less than about 0.02 (cgs units), in the range of cobalt ions in solution. All of these data are consistent with an organometallic complex where the metal is not highly condensed into a central core. The complex is dark brown in color and ultraviolet-visible spectroscopy reveals a spectrum that decreases from high absorbtion at 240 nm (the shortest wavelength measured) to low absorbtion at 600 nm, with peaks or shoulders at approximately 380 and 450 nm; one form shows a shoulder at about 364 nm. Larger cobalt and nickel complexes can also be synthesized. These have peaks or shoulders at longer wavelengths, about 520 to 540 nm, and are orange or red in color. If dried or precipitated by the addition of a base to the solution, the resulting particulates exhibit motion in an inhomogeneous magnetic field. When stored in water at room temperature, the cobalt complex exhibits no apparent change in properties, over a period of several months. Not only is the material highly water soluble, but it is not "sticky" and does not adhere to glass surfaces or proteins, such as albumin. The extended complex runs as a single peak on a gel filtration column in aqueous buffer, and run as a single spot on a TLC (thin layer chromatography) plate in 50:50 methanol:water. Ion exchange chromatography is able to separate several related charged species, indicating that the extended complex product is not a completely homogeneous mixture. These unusual characteristics distinguish this new magnetic material from others previously described.

The nickel extended complex is less stable than the extended cobalt complex. It exhibits alteration in its properties over time, and generally a partial reversal of formation after several hours. However, the nickel complex can be stabilized by crosslinking the organic moiety of the complex.

Due to its unique properties, the extended complex is useful for a variety of applications, most of which utilize aqueous solutions. The stability is a valuable asset to almost all uses. The non-aggregation of the complex particles is particularly significant to their use. Aggregated material exhibits altered properties, size control is difficult, purification is hampered, and control, when molecularly manipulating the extended complex, is generally lost. The extremely small size of the complex, 0.5–10 nm, makes it ideal for in vivo use, for forming ultrathin layers or coatings, and for rapid diffusion into materials. Since the complex does not stick to albumin and many other proteins, it can be used in vivo or in vitro without unwanted non-specific adhesion leading to background or altered biodistributions. The highly colored nature of the extended complex particles make them ideal for direct visualization and staining, in the absence of radioactive tags or other secondary enhancement procedures. The extended complex is made of cobalt or nickel, instead of other more magnetic materials commonly used, such as iron oxides and gadolinium. By comparison, the toxicity of cobalt is extremely low, which can be used to considerable advantage in in vivo applications in that larger amounts of complex can be administered.

The distributed disposition of the metal atoms in the extended complex makes the material ideal for use in several applications. Because the cobalt and nickel atoms are generally dispersed over the complex rather than in a dense central core, they are superior to other magnetic materials commonly used in the art for a variety of reasons. For example, in the procedure of MRI, contrast enhancement agents at the site of imaging alter relaxation times of adjacent water protons. The greatest effect is obtained when the magnetic atom is in intimate contact with the water molecules. Because the extended complex permits access of the water to more metal atoms, it serves as a far more effective enhancement agent than a material which contains a solid sphere, where internal atoms are shielded from water molecules. In this regard, the extended complex of the present invention provides improved MRI enhancement compared to a solid particle which has the same number of magnetic atoms.

The organic peptide component of the extended complex facilitates covalent conjugation to other molecules, such as binding moieties (e.g., antibodies and receptors). Linkage of an extended complex to another molecule confers magnetic properties to the linked product. An extended complex linked to another molecule, such as an antibody, peptide, nucleic acid, carbohydrate, or protein, is useful for instance, in targeting the extended complexes to specific molecules (e.g., in the identification of tumors, atherosclerotic plaques, clots, or specific extracellular matrix components, tissues, or cells). Methods for creating the linkage are discussed below.

Because extended complex contains multiple cobalt and/or nickel atoms, more of these magnetically active atoms can be delivered to a target by a single linked antibody, as compared to similar agents composed of antibodies linked to only one or a few magnetic atoms (e.g., antibodies linked to gadolinium). When labeling (also referred to herein as targeting) an antigen with a magnetic material, the amount of magnetic material delivered to a target is directly proportional to the signal which can be obtained, or the therapeutic effect which can be produced. Thus, sensitivity and efficacy in targeted delivery for imaging or therapy, is enhanced by use of the magnetic complex. In vitro labeling is similarly improved over use of single magnetic atom labels. For material applications, such as in sensors or coatings, the density of magnetic atoms also correlates with product quality.

One such use of the extended complex is in generating heat at a specific site within a matrix. This is produced by delivering the extended complex to the target site and then applying an oscillating magnetic field to remotely heat the magnetic particles. This produces selective heating in a matrix of only regions that contain the magnetic particles. For material applications, use of the extended complex of this invention may aid in nanofabrication, selective polymerization, and other uses where localized heating is required. For in vivo therapy, delivery of the extended complex, preferably targeted with a binding moiety to tumors or other tissues, atherosclerotic plaques, or extracellular matrix components that necessitate removal or alteration, followed by the application of a magnetic field to elevate the temperature in these specific regions, will cause cell death, or other heat-related responses, at that location. This modality of therapy is not currently available clinically due to problems with presently available magnetic materials, such as delivery, toxicity, side effects, and insufficient production of a response. However, use of the extended complex, especially use of a targeted extended complex, overcomes many of these difficulties by enabling large amounts of non-toxic magnetic material to be specifically targeted to the site of interest.

Another aspect of the present invention relates to a method for coupling other molecules to the extended complex. Several methods have been developed for linking other molecules to the extended complex, thus providing flexible protocols for the attachment of a variety of substances. A preferred method is to link the extended complexes to a Fab' antibody fragment that has one or more free hinge thiols. In the method, the Fab' antibody fragment is added to the extended complex synthesis reaction prior to addition of the thiol peptide. The metal is then complexed with the thiols, incorporating the Fab' during formation of the extended complex. This is a unique method, specific to the synthesis of these particles, and has not been described elsewhere. This method is rapid in that it does not require lengthy steps or purifications. Stable conjugates form in only a few seconds. Similarly, other molecules containing thiol groups can also be coupled to the extended complex by such incorporation in the synthesis reaction.

An alternative method for linking the extended complex to other molecules is to covalently couple the desired molecule to other functional groups (e.g., amino groups, carboxyl groups, or thiol groups) present on the preformed extended complex. For example, the alpha amino group of the thiol peptide may be linked by standard crosslinking reagents, such as the use of hydroxysuccinimide esters. Coupling to thiol groups may be by use of maleimides, and carboxyl groups may be linked with carbodiimides (e.g., 1-ethyl-3-(3-dimethylaminopropyl)carbodiimide (EDC)) or other such reactions. Other reactive groups and linking agents known in the art may also be utilized.

Therefore, coupling of additional molecules can be done before or after the complex is formed. By these methods, virtually any other molecules or surfaces may be covalently attached to the complex. Useful molecules to attach are Fab', IgG, peptides, hormones, dyes, proteins, nucleic acids, carbohydrates, lipids, nucleic acids, polymers, and glass.

Another aspect of the present invention relates to in vivo imaging tissue of an individual via magnetic resonance imaging using the extended complex (cobalt and/or nickel, or other alloys) as a contrast enhancement agent. To image the tissue of an individual, extended complex molecules are administered to the individual by a method which promotes contact of the agent to the tissue of the individual which is to be imaged. Following administration, magnetic resonance imaging is performed on the individual by methods standard in the art.

Imaging a tissue of an individual is described herein. However, it will be recognized by one of skill in the art that the present invention may be used to image a variety of internal components of an individual, including, without limitation, tissues, organs, cells, blood, extracellular matrix components, deposits, such as amyloid plaques and atherosclerotic plaques, inclusions, and other internal structures of the body, by the same methods described herein.

The method of administration of the extended complex molecules depends upon the location of the tissue which is to be imaged, and is easily determined by the skilled practitioner. Administration, for example may be via intraperitoneal injection, intravenous injection, intramuscular injection, and oral administration. The amount of the extended complex administered will depend upon the sensitivity of the machine used for magnetic resonance imaging, as well as other variables, and will be determined by the skilled practitioner for each specific application. As a general rule of thumb, an amount from 0.1 to 10 mg of contrast enhancement agent per kilogram of body weight of the individual is preferred. These amounts, however, should not be seen as limiting to the present invention.

This method for in vivo imaging is suitable for any animal in which magnetic resonance imaging is usually performed. In a preferred embodiment, the individual is human. Tissues suitable for imaging by this method include, without limitation, skeletal, secretory, digestive, muscular, reproductive, circulatory, immunological, neurological, and tumor tissue. Some specific examples of tissues for imaging are liver, pancreas, kidney, veins, arteries, lung, heart, brain, breast, colon, lymph nodes, alimentary tract, and prostate.

In vivo imaging of a tissue by the above described method is particularly useful for identifying a tumor in an individual, and can be used for routine diagnostic screening. In one embodiment, the tumor is a brain tumor. As detailed in the Exemplification section below, use of extended cobalt complex as a contrast enhancement agent allowed detection of brain tumors in rats which were not otherwise detectable using gadodiamide, a standard contrast enhancement agent used in the art.

To facilitate specific targeting of a tissue or other internal component, by the contrast enhancement agent, the extended complex may be operably linked to a moiety which has an affinity for a component unique to the imaged tissue or component, or is otherwise localized or channeled to the region of the imaged tissue by bio-processes of the individual. Such a moiety can be a useful biomolecule (e.g., an antibody fragment which binds antigen, an antibody, a polypeptide, a nucleic acid, a carbohydrate, or a lipid), a drug, or a synthetic molecule specifically engineered or designed for tissue targeting. In one embodiment, the moiety is a binding moiety which specifically binds, or is bound by, the molecular marker. Highly useful binding moieties are members of a specific binding pair, (e.g., antibody-antigen, receptor-ligand, hybridizing nucleic acids). Such binding is necessary under physiological conditions with sufficient affinity to anchor the attached cobalt complex to the molecular marker during imaging. The term "operably linked", as used herein, is used to indicate that the basic functions of the components in the linkage (contrast enhancement agent and binding moiety) are preserved Thus, the extended complex retains function as a contrast agent and the binding moiety retains its affinity for the molecular marker. Linkage of the extended complex to the binding moiety is by any means which stably, physically associates the binding moiety to the extended complex under physiological conditions. Preferably, the linkage is covalent. Methods for creating such a linkage are described above.

Molecular markers to which the extended complex may be targeted are preferably expressed on the cells which make up the target at significantly higher levels than elsewhere in the body. For example, prostate specific antigen is useful for imaging prostate tissue. Some useful molecular markers include, without limitation, receptors, oncoproteins, surface antigens, lipids, carbohydrates, and tumor antigens. Extended complex targeting is not limited to endogenous cells of the individual, in that a foreign cell or cell byproduct, (e.g., fungal cells) may be selectively targeted, for example, to aid in diagnosis.

The preferred time post administration for imaging is following a period of time in which unbound agent has appreciably cleared, as this generates an optimal signal to noise ratio. The time period is determined through routine experimentation and is within the ability of one of average skill in the art.

Another aspect of the present invention relates to a method for diagnosing the progression or functionality of a tumor in vivo by selectively imaging tumor tissue which expresses a particular molecular marker. Imaging of the tumor, which expresses the molecular marker, is performed with extended complex that is specifically targeted to the molecular marker via linkage to a specific binding moiety. In this way, the presence or absence of a marker for tumor progression (e.g., an oncogene) on the tumor is determined by magnetic resonance imaging. Similarly, targeted extended complex can be used to determine the presence of markers for other diseases which result in differential expression of surface antigens (e.g., viral infection). The binding moiety or other targeting agent, which is linked to the extended complex, targets the contrast enhancement agent to the location of the molecular marker. Targeting contrast enhancement agent for diagnostic purposes utilizing the extended complex is superior to the same approach using gadolinium, the sensitivity of which is limited by the amount of antigen present on the target. Because the extended complex is more potent, this procedure is more sensitive.

The extended complex of the present invention may also be used as a contrast enhancement agent in magnetic resonance imaging to image tissue which is regenerating from a wound. The method is performed essentially as that indicated above for in vivo imaging tissue in an individual, with specific identification of a regenerating wound being facilitated by increased contrast conferred by the extended complex contrast agent. As referred to herein, a wound is the result of a force or pathology which has caused damage to tissue to produce a tear, break, or abrasion. The portions of the wound which are imaged are the regions undergoing tissue regeneration and remodelling. Any damaged tissue may be thus imaged. For instance, skeletal (bone, cartilage) secretory, digestive, muscular, reproductive, vascular, circulatory, brain, breast, prostate, arterial, and heart tissue, which has been wounded and is regenerating can be imaged by this method. Imaging wounded tissue is useful for diagnostic purposes as well as monitoring the healing process. This is especially useful for internal injuries or lesions not easily observable by clinical inspection.

Another aspect of the present invention relates to the use of the extended complex, described above, in detecting the presence of a target molecule (e.g., an antigen) in a sample via visual or alternatively magnetic detection of accumulated extended complex. Experiments detailed in the Exemplification section below (Examples 5 and 6) indicate that molecules of the extended complex operatively linked to a specific binding moiety (e.g., an antibody), as discussed above, concentrate at the particular location of target molecule upon exposure to the target molecule. This concentration is visibly detectable, due to the characteristic color of the extended complex.

To detect the presence of a target molecule (e.g., antigen) in a sample, targeted extended complex specific for the target molecule is contacted to the sample under conditions appropriate for binding of target by the binding moiety. Optionally, the sample is then washed to remove unbound extended complex, thus improving the signal to noise ratio. The presence of extended complex which remains bound to the target is then identified by its characteristic properties (color or magnetic properties). The presence of the extended complex is an indication of the presence of the binding moiety and hence the presence of the target molecule. Preferably, the binding moiety is an antibody and the target molecule is an antigen to which the antibody binds.

The target molecule is necessarily bound by the specific binding moiety, or alternatively necessarily binds the specific binding moiety, with sufficient affinity that binding persists throughout the detection process (e.g., washing, and any process of detection employed). The minimal amount of target which can be detected is limited by the sensitivity of the color or magnetic detection. Sufficient amounts of accumulation are possible with microgram quantities of target molecule to be visible to the naked eye. Sensitivity of detection may be enhanced using an optical detection device to detect the specific color absorbtion wavelength of the extended complex, or using a magnetic detection device.

Sample may be an aqueous solution, or a non-aqueous sample (e.g., tissue). Detection is greatly facilitated by fractionation of the sample (e.g., by size) and/or immobilization of the sample onto a solid support (e.g., an immunoblot or ELISA). Such applications are highly suited for in vitro and in situ analysis.

Quantitative detection of the target molecule is possible with the targeted extended complex. For quantitative detection, standardized amounts of target molecule are used to calibrate the detection signal produced by the targeted extended complex. The amount of a target molecule in a sample is then determined by comparison of the detection signal generated from the sample to the calibrated signal obtained with the standards. Such calibration is routinely performed in the art and known to the skilled practitioner. This aspect of the present invention is extremely useful in one-step detection kits which presently utilize colloidal gold and colored latex particles/beads, such as the kind of kits currently marketed as home pregnancy tests.

Exemplification

The following examples are provided only as a sampling of the possibilities defined herein, and are not intended to be limiting, since variations, extensions, and applications will be obvious to persons skilled in the art.

EXAMPLE 1

Preparation of Organic Cobalt Complex

A solution of 20% (by weight) cobalt (II) chloride hexahydrate in 0.4 ml water was mixed with a 20% solution of (tri)sodium citrate in 0.4 ml $H_2O$. Next, 0.4 ml of 2 Molar ammonium hydroxide was added, and the red solution changed to a more pink/purple color. Next, 0.1 ml of an aqueous solution of 8% reduced glutathione was added, and the solution then turned dark brown. After 5 min, an additional aliquot, namely 0.05 ml of an aqueous solution of 8% glutathione was added, and the solution became darker in color.

The product was purified on a gel filtration sizing column packed with Amicon GH25, and run with water as the eluent. The complex appeared in the void volume and this step was used to remove any species less than about 3,000 apparent molecular weight, namely, any free cobalt ions or glutathione.

Fractions containing the complex were dried by vacuum rotary evaporation, then resuspended in a small amount of water. This permitted facile concentration of the product. Electron microscopy confirmed that 0.5 to 10 nm complex had formed.

EXAMPLE 2

Preparation of Organic Nickel Complex 0.2 ml of an aqueous 10% sodium citrate solution was added to 0.2 ml of a 10% aqueous nickel sulfate solution. Next, 0.2 ml of a 1 Molar ammonium hydroxide solution was added. Then 0.05 ml of a 4% aqueous glutathione solution was added and the mixture turned dark brown. After 5 minutes, an additional 0.05 ml of the 4% aqueous glutathione solution was added.

EXAMPLE 3

Preparation of 10 to 20 nm Organic Cobalt Complex 0.2 ml of an aqueous 10% sodium citrate solution was added to 0.2 ml of a 10% aqueous cobalt chloride solution. Next, 0.2 ml of a 10% ammonium chloride solution was added, followed by 0.2 ml of a 0.1% sodium hypophosphite aqueous solution. Next, 0.3 ml of a 1 molar ammonium hydroxide solution was added. Then 0.02 ml of a 4% aqueous glutathione solution was added and the mixture turned orange, and later matured over several hours into an orange-red then red solution. In another preparation, similar sized cobalt complex was formed by mixing 0.2 ml of an aqueous 10% sodium citrate solution with 0.2 ml of a 10% aqueous cobalt chloride solution, followed by addition of 0.4 ml of a 1 molar ammonium hydroxide solution, then addition of 0.05 ml of a 4% aqueous glutathione solution.

EXAMPLE 4

Preparation of Mixed Cobalt and Nickel Complex 0.1 ml of a 10% aqueous cobalt chloride solution was mixed with 0.1 ml of a 10% aqueous nickel sulfate solution. 0.2 ml of an aqueous 10% sodium citrate solution was then added. Next, 0.2 ml of a 1 molar ammonium hydroxide solution was added. Then 0.05 ml of a 4% aqueous glutathione solution was added and the mixture turned brown. After 5 minutes, another 0.05 ml of the 4% aqueous glutathione solution was added.

EXAMPLE 5

Covalent Linking of Antibody to Organic Cobalt or Nickel Extended Complex During their Preparation, and Targeting of the Complex to an Antigen Fab' antibody fragments were prepared by reducing 0.2 mg of rabbit anti-mouse antibodies which specifically bind mouse IgG with 30 mM dithiothreitol (DTT) in 0.1 molar phosphate buffer, pH 6 containing 5 mM EDTA (ethylenediamine tetraacetic acid) for 1 hr. Fab' antibody fragments were then purified from DTT and other low molecular weight components on a gel exclusion column (Amicon GH25) running with water as the eluent. The protein peak was pooled into a 2 ml volume.

Cobalt or nickel complex was prepared by mixing a solution of 20% (by weight) cobalt chloride or nickel sulfate in 0.4 ml water with a 20% solution of (tri)sodium citrate in 0.4 ml water. Next, 0.4 ml of 2 Molar ammonium hydroxide was added. Several identical preparations up to this point were made. To some, 1 ml of the purified Fab' antibody solution was added, containing about 0.08 mg of antibody; to others, 0.3 ml of Fab' was added, and others 0.03 ml, and others no antibody was added. 0.1 ml of an aqueous solution of 8% glutathione was added to each reaction, and the solutions then turned dark brown. After 5 min, an additional aliquot, namely 0.05 ml of an aqueous solution of 8% glutathione was added, and the solutions became darker in color.

Although further purification or optimization of reaction amounts and times could have been done, the samples were used immediately. They were all diluted to 2 ml, and 1 ml of each was applied to individual nitrocellulose membranes to which was bound 5 micrograms of mouse IgG (the target antigen). The nitrocellulose membranes had previously been dried and blocked with 4% serum albumin. After 5 minutes, the samples generated with the highest amount of rabbit anti-mouse Fab' produced a brown coloration at the location of the antigen. This indicated targeting of the antibody linked complex to the antigen. Samples generated with lower amounts of Fab' also produced a brown coloration at the location of antigen, however this coloration was concomitantly weaker and took longer to develop (it was obvious after 10 minutes). The samples generated with no Fab' produced no coloration of the antigen, indicating that the complex without the antibody did not exhibit significant non-specific binding to the antigen. The fact that no significant brown coloration was detected on the albumin coated membrane at regions which did not contain antigen, indicates that the complex, with or without antibody had no significant affinity for albumin.

EXAMPLE 6

Covalent Linking of Antibody to Organic Cobalt or Nickel Extended Complex after Preparation, and Targeting of the Complex to an Antigen Cobalt or nickel organic complex were prepared and purified as described in Examples 1 through 3 above. The free amino groups of the organic peptide in the particles was linked to by mixing with a molar excess of bis (sulfosuccinimidyl) suberate. After 30 min, the particles were purified from excess reagent by gel exclusion chromatography. Rabbit anti-mouse IgG was added and incubated overnight at 4 degrees C. The particles then demonstrated immunotargeting to their appropriate antigen, using the blot method of Example 5. This showed that the particles could be covalently coupled using the amino groups of the organic moiety, and could be linked to molecules containing free amino groups.

EXAMPLE 7

Demonstration of Magnetic Properties of the Extended Cobalt Complex

Extended cobalt complex was prepared as described in Example 1. The complex was precipitated by adding additional amounts of glutathione or by addition of sodium hydroxide. The brown precipitate at the bottom of the aqueous solution was then placed near a pole edge of a magnetron magnet, and the particles were drawn to the magnet pole in this inhomogeneous field.

Conclusion

The above described experiments detail the production of a new class of extended organic cobalt and nickel magnetic complex with unique properties and a process for synthesizing them. Also included is a mixed cobalt and nickel extended complex. The organic moieties permit convenient covalent linking to antibodies, peptides, proteins, carbohydrates, lipids, nucleic acids, or other organic or inorganic molecules by conventional crosslinking technology. A novel incorporation of Fab' antibody fragments, or other thiol compounds during the complex synthesis is also described. These provide a way of targeting the magnetic complex to sites of interest, in vivo or in vitro, or for coating surfaces, or for inclusion into polymers or other materials. A method of controlling the size of the particles has also been discovered.

The ramifications of this new class of magnetic materials are far reaching since magnetic materials have been found to be useful in many areas including sensors, computer storage, magneto-optical devices, medical imaging and therapy.

EXAMPLE 8

MRI of Brain Tumors using Cobalt Complex

Rats were implanted with tumors by stereotactic infusion of tumor cells into the brain. After 14 days, brain scan magnetic resonance images were taken using both the standard gadolinium contrast agent gadodiamide (Omniscan, Nycomed) and the cobalt complex of the present invention. Two rats, each implanted with the same tumor (either N32 or F98) were imaged side-by-side using either gadodiamide or cobalt complex as the contrast agent. No enhancement of either brain tumor (N32 and F98) was seen with the gadodiamide. Tumors could not be located via MRI using this agent. However, the tumors were clearly imaged using the cobalt complex as contrast agent. These images had excellent contrast. On day 18, the rats were dissected to demonstrate that equivalent tumors existed in all animals. Thus, differential tumor development was not a factor in the differential tumor detection of the gadodiamide versus the cobalt complex. The results obtained using the gadolinium is reflective of its usage in humans for tumor visualization, whereby the gadolinium agents facilitate imaging for some tumors, but are unsatisfactory for many others.

Various MRI imaging modes were used in the analysis: T1-weighted, T2-weighted, and T2*-weighted. In all cases the tumors were clearly visible using cobalt complex, but no trace of any tumors was evident using the gadodiamide. Importantly, good image contrast was retained up to 30 minutes post injection of the cobalt complex, at which time imaging was concluded. This minimal change in image contrast over the imaging time indicates that useful imaging can be accomplished well beyond this time point. This is in contrast to gadolinium images, which in general are much more transitory due to the fact that the gadolinium agents clear the system rapidly. This longevity indicates that cobalt complex can be used for imaging over extended periods of time (e.g., during surgery), currently not possible with the gadolinium agents.

EXAMPLE 8 METHODS

Tumor Implantation.

Two cell lines were used to seed the tumors: F98 and N32 (Barth, R. F., *J. of Neuro-Oncology* 36: 91 (1998); Siesjo et al., *Cancer Immunol. Immunother.* 37: 67 (1993)). Rats weighing about 350 g, seeded with either F98 or N32 cells were used for tumor imaging. A<0.5 mm burr hole was drilled through the skull of the anesthetized rats at the point of inoculation. Tumors were initiated by inoculating one microliter of culture medium, containing 10,000 cultured cells, 4–5 mm deep into the left striatum, at a point 4 mm to the left of the midline in the (serrated) coronal suture. A 27-gauge needle fitted with a depth-limiting plastic collar to ensure cell injection 4–5 mm beneath the skull was connected to a Hamilton microsyringe via flexible tubing. Following a 30-second infusion of the cells, another 30 seconds was taken to allow the cells to settle before removing the needle. For F98 tumor animals, death ensued 24+ days after inoculation.

Cobalt Complex: Cobalt Complex was Prepared as in Example 1.

MRI.

MRI was performed at day 16 after tumor cell implantation. The animals were anesthetized and injected interperitoneally with either 200 microliters of gadodiamide (287 mg gadodiamide/ml) (Omniscan, Nycomed, Princeton, N.J.) or 200 microliters of the extended cobalt complex (containing 10 mg Co/ml ±30%). The rats were immediately positioned on a support and MRI was performed in a 1.5 tesla whole-body clinical scanner (Siemens Vision, Germany) with a human extremity (knee) coil. High-resolution turbo spin-echo sagittal imaging was used for selecting slice position with imaging parameters as follows. For T2 weighted images: repetition time (TR)=3000 msec; echo time (TE)= 25 msec; field of view (FOV)=100×100 mm; matrix size= 256×256; image slice thickness (TH)=2 mm. Tumor images were collected at various times after a single interperitoneal injection. Imaging times were 3 min/scan and resolution was 0.3125 nm. Imaging covered a 30 min period after injection.

Two rats were imaged simultaneously, one with gadodiamide, and one with cobalt reagent. T2 weighted imaging seemed to be slightly better. T1 weighted and T2* weighted images gave comparable results. Tumor contrast was still evident 30 min after injection.

EXAMPLE 9

Wound Healing Delineation by MRI using Cobalt Complex

MRI of the rats implanted with tumors in Example 8 using cobalt complex as contrast agent revealed image contrast at the site which had been opened two weeks prior to injecting the tumor cells. This site appeared white in the images, and was very well contrasted. No such contrast was evident at the corresponding site in images produced with the gadodiamide contrast agent. This indicates that regions of wound healing (e.g., revascularization, clotting, remodelling, clot dissolution, and tissue regrowth) can be clearly imaged with the cobalt complex. This is surprising as the vasculature and components of a wounded region differ from normal tissue only subtly, and these differences are not highlighted by the gadodiamide reagent. This type of imaging can be used to detect internal damage, internal bleeding, or other forms of lesions with MRI using the cobalt complex as contrast agent.

EXAMPLE 9 METHODS

Methods were performed as in Example 8.

EXAMPLE 10

Toxicity Measurement of Cobalt Complex

Blood analysis was performed on rats which received the cobalt complex or the gadodiamide to study toxicity of the two contrast agents. Analysis was performed on: 1) a control rat, 2) a rat after injection of the gadodiamide, and 3) a rat after injection of the cobalt complex. Standard hematology and blood chemistry indicators commonly used to indicate toxicity were measured by standard methods. These indicators were glucose (GLUCm), blood urea nitrogen (BUNm), creatine (CREm), sodium (NA), potassium (K), chloride (CL), carbon dioxide (CO2), creatine kinase (CK), aspartate transaminase (AST), alanine transaminase (ALT), alkaline phosphatase (ALP) and albumen (ALBm) levels. Results are presented in Table 1, below. A slight increase in liver enzyme activity compared to the control was observed for the rats injected with the cobalt complex or gadodiamide. The observed elevation was greater for the gadodiamide injected rat than for the cobalt complex injected rat. Overall, there was no discernable toxicity of the cobalt complex compared to the gadodiamide, which is accepted to be non-toxic.

TABLE 1

|  | control rat | + gadodiamide | + cobalt |
|---|---|---|---|
| GLUCm | 250 mg/dL | 177 | 210 |
| BUNm | 12 mg/dL | 16 | 12 |
| CREm | 0.3 mg/dL | 0.2 | 0.3 |
| NA | 139 mEq/L | 139 | 138 |
| K | 4.0 mEq/L | 5.5 | 4.0 |
| CL | 101 mEq/L | 101 | 103 |
| CO2 | 31 mEq/L | 30 | 23 |
| CK | 531 IU/L | 820 | 795 |
| AST | 73 IU/L | 183 | 128 |
| ALT | 35 IU/L | 62 | 41 |
| ALP | 187 IU/L | 202 | 252 |
| ALBm | 1.7 g/dL | 1.5 | 1.5 |

EXAMPLE 10 METHODS

Rats were seeded with tumor as described in Example 8. The normal rat was seeded with the N32 tumor, and the rats which received either gadodiamide or cobalt complex were seeded with the F98 tumor. The gadodiamide and cobalt complex was delivered by IP injection. Blood was drawn 1 day after injection of the agents, allowed to sit and clot at room temperature for 20–30 min, then centrifuged at 3500 rpm. The clear serum was frozen at −20° C. Serum was then analyzed for GLUCm, BUNm, CREm NA, KCl, CO2, CK, AST, ALT, ALP, and ALBm by standard methods. Data are derived from one of each test rat. These results were verified in additional rat subjects.

What is claimed is:

1. A method for in vivo imaging tissue of a individual, comprising:
   a) providing an extended cobalt complex which comprises cobalt atoms, a carboxylate ligand, an amine ligand, and a multidentate thiol-containing organic ligand, the cobalt atoms being linked to thiol groups and counter ions, the extended complex being characterized as:
      i) stable;
      ii) water soluble;
      iii) non-aggregating;
      iv) magnetic; and
      v) from 0.5 to 10 nm in size;
   b) administering the extended cobalt complex of step a) to the individual to contact the tissue with the extended cobalt complex; and
   c) performing magnetic resonance imaging on the individual to image the tissue.

2. The method of claim 1 wherein the tissue is a tumor.

3. The method of claim 1 wherein the tissue is regenerating from a wound.

4. The method of claim 1 wherein the tissue is bone, muscle, cartilage, liver, pancreas, kidney, veins, arteries, lung, heart, brain, breast, colon, lymph nodes, alimentary tract, and prostate.

5. The method of claim 1 wherein the individual is human.

6. The method of claim 1 wherein the individual is an animal.

7. A method for identifying a tumor in an individual comprising:
   a) providing an extended cobalt complex which comprises cobalt atoms, a carboxylate ligand, an amine ligand, and a multidentate thiol-containing organic ligand, the cobalt atoms being linked to thiol groups and counter ions, the extended complex being characterized as:
      i) stable;
      ii) water soluble;
      iii) non-aggregating;
      iv) magnetic; and
      v) from 0.5 to 10 nm in size;
   b) administering the extended cobalt complex of step a) into the individual to contact the tumor with the extended cobalt complex; and
   c) performing magnetic resonance imaging on the individual to identify the tumor.

8. The method of claim 7 wherein the individual is human.

9. The method of claim 7 wherein the individual is an animal.

10. The method of claim 7 wherein the extended cobalt complex is linked to a targeting molecule.

11. The method of claim 10 wherein the targeting molecule is selected from the group consisting of an antibody fragment, an antibody, a polypeptide, a nucleic acid, a carbohydrate, and a lipid.

12. The method of claim 7 wherein administering step b) is by a form of administration selected from the group consisting of intraperitoneal, intravenous, intramuscular, and oral.

13. A method for in vivo imaging tissue in an individual, wherein the tissue is regenerating from a wound, comprising:
   a) providing an extended cobalt complex which comprises cobalt atoms, a carboxylate ligand, an amine ligand, and a multidentate thiol-containing organic ligand, the cobalt atoms being linked to thiol groups and counter ions, the extended complex being characterized as:
      i) stable;
      ii) water soluble;
      iii) non-aggregating;
      iv) magnetic; and
      v) from 0.5 to 10 nm in size;

b) administering the extended cobalt complex to the individual to contact the tissue with the extended cobalt complex; and c) performing magnetic resonance imaging on the individual to image the wounded tissue.

14. The method of claim 13 wherein the tissue is selected from the group consisting of skeletal, secretory, digestive, muscular, reproductive, circulatory, and, immunological, neurological.

15. The method of claim 13 wherein the tissue is selected from the group consisting of liver, pancreas, kidney, veins, arteries, lung, heart, brain, breast, colon, lymph nodes, alimentary tract, and prostate.

16. A method for in vivo imaging a tissue in an individual, wherein the tissue expresses a specific molecular marker, comprising:

a) providing an extended cobalt complex which is functionally linked to a binding moiety specific for the molecular marker, wherein the extended cobalt complex comprises cobalt atoms, a carboxylate ligand, an amine ligand, and a multidentate thiol-containing organic ligand, the cobalt atoms being linked to thiol groups and counter ions, the extended complex being characterized as:
   i) stable;
   ii) water soluble;
   iii) non-aggregating;
   iv) magnetic; and
   v) from 0.5 to 10 nm in size;

b) administering the extended cobalt complex of step a) to the individual to contact the molecular marker of the tissue with the extended cobalt complex; and c) performing magnetic resonance imaging on the individual to image the tissue which expresses the molecular marker.

* * * * *